United States Patent
Brown et al.

(10) Patent No.: US 8,041,420 B2
(45) Date of Patent: Oct. 18, 2011

(54) APPARATUS FOR MEASURING TISSUE SAMPLES ELECTRICAL IMPEDANCE

(75) Inventors: Brian Hilton Brown, Derbyshire (GB); John Anthony Tidy, Sheffield (GB)

(73) Assignees: The University of Sheffield, South Yorkshire (GB); Sheffield Teaching Hospitals NHS Foundation Trust, Sheffield (GB)

( * ) Notice: Subject to any disclaimer, the term of this patent is extended or adjusted under 35 U.S.C. 154(b) by 119 days.

(21) Appl. No.: 11/916,383

(22) PCT Filed: Jun. 2, 2006

(86) PCT No.: PCT/GB2006/002038
§ 371 (c)(1),
(2), (4) Date: Dec. 3, 2007

(87) PCT Pub. No.: WO2006/129116
PCT Pub. Date: Dec. 7, 2006

(65) Prior Publication Data
US 2008/0262375 A1    Oct. 23, 2008

(30) Foreign Application Priority Data
Jun. 3, 2005    (GB) .................................. 0511323.8

(51) Int. Cl.
*A61B 5/05*    (2006.01)
(52) U.S. Cl. .................................................. 600/547
(58) Field of Classification Search .................. 600/547
See application file for complete search history.

(56) References Cited

U.S. PATENT DOCUMENTS

| | | | | |
|---|---|---|---|---|
| 4,820,399 A | * | 4/1989 | Senda et al. | 435/817 |
| 5,991,650 A | * | 11/1999 | Swanson et al. | 600/372 |
| 6,071,278 A | * | 6/2000 | Panescu et al. | 606/41 |
| 6,690,181 B1 | | 2/2004 | Dowdeswell et al. | |
| 2001/0007071 A1 | | 7/2001 | Koblish | |
| 2003/0105411 A1 | * | 6/2003 | Smallwood et al. | 600/547 |

FOREIGN PATENT DOCUMENTS

| | | |
|---|---|---|
| DE | 2736623 | 3/1978 |
| EP | 0598459 | 5/1994 |
| FR | 2712498 A1 | 5/1995 |
| FR | 2754717 A1 | 4/1998 |
| WO | 9841151 | 9/1998 |
| WO | 0167098 | 9/2001 |
| WO | WO 2004/084872 | * 10/2004 |
| WO | 2004098389 | 11/2004 |

OTHER PUBLICATIONS

Brown B H et al: "Relation Between Tissue Structure and Imposed Electrical Current Flow in Cervical Neoplasia", Lancet. Mar. 11, 2000, vol. 355, No. 9207, pp. 892-895, ISSN: 0140-6736, XP004821382.

(Continued)

*Primary Examiner* — Max Hindenburg
*Assistant Examiner* — Emily Lloyd
(74) *Attorney, Agent, or Firm* — Kirton & McConkie; Evan R. Witt

(57) ABSTRACT

Apparatus for measuring the electrical impedance of a tissue sample comprises a probe and a sheath comprising an elongated tubular body having one closed end and one open end providing an internal cavity. The sheath is composed of a material which when contacted with a tissue sample is capable of providing a conductive path through the sheath between the electrodes and the tissue sample. The resistivity of the material forming the sheath when contacted with the tissue sample is greater than the resistivity of the tissue sample. The probe is received within the internal cavity of the sheath. The sheath is impervious to bacteria and viruses.

9 Claims, 1 Drawing Sheet

OTHER PUBLICATIONS

Brown B H et al: "Bipolar and Tetrapolar Transfer Impedance Measurements from Volume Conductor", Electronic Letters, Dec. 7, 2000, vol. 36, No. 25, pp. 2060 to 2062.

Cleveland Christopher T., "Standardized Membrane Pore Size Characterization by Polyethylene Glycol Rejection", Journal of Environmental Engineering, vol. 128, Issue 5, pp. 399 to 407 (May 2002).

* cited by examiner

APPARATUS FOR MEASURING TISSUE SAMPLES ELECTRICAL IMPEDANCE

BACKGROUND OF THE INVENTION

The present invention provides apparatus for measuring the electrical impedance of a tissue sample.

It is known that certain medical conditions can be monitored by measuring the impedance of a patient's tissue. This can be done by applying electrodes to the tissue through which a low voltage current can be passed through the tissue. It is known to use this technique to detect abnormal cell growth which can be indicative of a tumour. Electrical impedance spectroscopy has been used to identify premalignant changes in tissue samples, especially to identify the pre-cancerous phase of cervical cancer, known as cervical intraepithelial neoplasia (CIN).

Impedance measurements can be used to detect other conditions of a patient. For example, onset of labour is accompanied by changes in tissue impedance which can be identified by such measurements.

Electrical impedance spectroscopy measures the electrical impedance spectra of superficial tissues, such as for example cervical epithelium by placing an electrically conductive probe in contact with the tissue sample. Biological tissues have an electrical impedance which is dependant on the frequency of the current passed through the tissue. The biological tissues contain a number of components, such as a nucleus and a cytoplasm which have both resistive and capacitive properties. It is known that in cancerous and pre-cancerous tissues there is a significant change in the size of the cell nuclei, in the shape of the cells and in the arrangement of cells which form the tissue. These changes affect the electrical impedance of the tissue sample and therefore electrical impedance tomography can be used to detect significant changes in cell structure and therefore diagnose patients suffering from CIN.

The magnitude of the electrical impedance and the dependence of the electrical impedance on frequency of a tissue sample have been found to be indicative of the tissue composition. It has been found that different tissue structures are associated with different frequency bands within an electrical impedance spectrum.

It has been found that at low frequencies (less than about 1 kHz) the current is unable to pass through the cells due to the capacitance of the cellular membrane and charge accumulation occurs at large membrane interfaces. At intermediate frequencies, such as in the region of about 1 kHz to 1 MHz (also known as the β dispersion region) cell structures are the main determinant of tissue electrical impedance and current begins to penetrate the cell membranes. However, at higher frequencies (greater than about 1 MHz) the current is able to pass through the cells and the nuclei and at even higher frequencies (>1 GHz) the molecular structure is the determining factor contributing towards the electrical impedance of the tissue sample.

Within the lower part of the β dispersion range, low frequency current can be considered to be passing through the extracellular space within the tissue sample. The current passes around the cells and the resistance to the flow of the current will therefore depend upon the cell spacings and how the cells are arranged. At higher frequencies however current can penetrate the cell membranes and pass through both the intracellular and extracellular spaces. The current will therefore pass into the cells and the resistance to current flow will be determined by intracellular volume and possibly the size of the nucleus.

It is known that by measuring the electrical current patterns produced by a tissue sample over a range of frequencies, and applying an inverse modelling procedure, electrical parameters resulting from the tissue structure may be determined. The intracellular resistance of a given tissue sample has been found to be significantly affected by the relative sizes of the nucleus and the cell. It has therefore been found that the electrical impedance of tissue samples can be used to distinguish between tissues having different nuclear volume to cytoplasm volume ratios. Tissue samples having a higher ratio of nuclear volume to cytoplasm volume may be indicative of pre-cancerous tissues. The application of electrical impedance measurements using a probe which bears four electrodes on an end face in cervical cytology is disclosed in Electronics Letters, 36 (25) 2060-2062 and in The Lancet, 355: 892-95.

For example, it is known that in cervical tissues the major changes in the pre-cancerous stages are the gradual breakdown of superficial cell layering and the increase in the size of the cell nuclei. These changes will therefore have an effect on the electrical impedance of a tissue sample at intermediate frequencies and therefore electrical impedance can be used to diagnose the presence of pre-cancerous tissues.

The electrical impedance of a tissue sample is measured to give mean values of electrical impedance at a number of frequencies. This data, forming an electrical impedance spectrum, is then fitted by a least square deviation method to a Cole equation as discussed in US-2003/0105411 of the form:

$$Z = R_\infty + \frac{(R_0 - R_\infty)}{(1 + (jF/F_c)^{(1-\alpha)}}$$

to give estimates of $R_0$, $R_\infty$ and $F_c$. $R_0$ and $R_\infty$ are the electrical impedances of the tissue sample at very low and very high frequencies respectively, $F_c$ is a frequency and $\alpha$ is a constant. $\alpha$ increases with the inhomogeneity of the tissue however it can be assumed that $\alpha$ is zero to improve the accuracy in the estimation of $F_c$. In this case an equivalent electrical circuit consisting of a resistor R placed in parallel with a resistor S and capacitor C in series will have an impedance Z, given by the above equation, where:

$$R_0 = R, \quad R_\infty = \frac{RS}{R+S}, \quad F_c = \frac{1}{2\pi C(R+S)}$$

Parameters R, S and C can therefore be determined from the fitted Cole equation. Because the probe was calibrated in saline of known conductivity, R and S are inversely proportional to conductivity and have the units of Ωm. R and S can therefore be related to the extracellular and intracellular spaces respectively. C is related to the cell membrane capacitance and is given in units of $\mu F \cdot m^{-1}$.

WO-01/67098 discloses the use of an electrically conductive probe for measuring the electrical impedance of tissue samples comprising a tetrapolar electrode arrangement positioned at the probe tip for the in vivo measurement of the electrical impedance spectra of a tissue sample. Subject matter disclosed in that document is incorporated in the specification of the present application by this reference.

SUMMARY OF THE INVENTION

Known electrical probes have certain disadvantages. The probe must be sterilised after use, for example by cleaning chemicals. The sterilisation of the probes is both costly and time consuming. The screening unit must therefore obtain a significant number of probes so that while used probes are in the process of being sterilized there are enough sterilized probes available to screen the desired number of patients.

WO-98/41151 discloses a discardable, sterile sheath for use on a probe that performs both optical and electrical measurements. The sheath comprises electrodes on the tip of the sheath in close proximity to an optical window provided by the sheath. The electrodes on the tip of the sheath are close to the optical window to ensure that both optical and electrical measurements can be performed on the same area of tissue. The internal probe comprises electrical connections which make electrical contact with the electrodes in the sheath. However, any failure in electrical contact between the electrical connections of the probe and the electrodes in the sheath will lead to false readings which may lead to the incorrect diagnosis of a patient. There is therefore an undue burden placed on the operator in connecting the probe sheath to the probe correctly so as to provide an accurate measurement of the electrical impedance of the tissue sample. The provision of electrodes on the disclosed sheath also means that it is expensive to manufacture.

The present invention provides apparatus for measuring the electrical impedance of a tissue sample, which comprises:
(a) an elongate probe having electrodes towards one end thereof through which an electrical signal is transmitted between the apparatus and tissue in contact with it; and
(b) a sheath comprising an elongate tubular body having a closed end and an open end and defining an internal cavity, in which the end of the probe on which the electrodes are provided can fit into the cavity, and in which at least a portion of the sheath is formed from a material which when contacted with a tissue sample is capable of providing a conductive path through the sheath between the electrodes and the tissue sample, and in which the resistivity of the material when contacted with the tissue sample is greater than the resistivity of the tissue sample.

The sheath can be formed at least partially from a non-electrically conductive polymeric material with a porous structure such that it can be impregnated with body fluid when contacted with a tissue sample and provides an ionically conductive path through the sheath between the electrodes and the tissue sample.

The sheath can be formed at least partially from a material which is inherently electronically conductive. For example, it can be formed from a material which is loaded with a conductive filler. Examples of suitable conductive fillers include certain carbon blacks.

Preferably, the ratio of the resistivity of the material of the sheath (when impregnated with body fluid if the conductivity through the sheath relies on ionic conduction in the body fluid) to the resistivity of the tissue sample is at least about 10, more preferably at least about 50, especially at least about 100, more especially at least about 500, for example at least about 1000.

It is known that the typical electrical resistivity of a tissue sample is about 1 $\Omega$m. Preferably, at least a portion of the sheath is composed of a material which when contacted with a tissue sample has a resistivity of greater than about 1 $\Omega$m, preferably greater than about 500 $\Omega$m, for example greater than about 1000 $\Omega$m. Preferably, at least a portion of the sheath is composed of a material which when contacted with a tissue sample has a resistivity of less than about 5000 $\Omega$m, more preferably less than about 4000 $\Omega$m, for example less than about 2500 $\Omega$m.

A probe can be calibrated by placing them in contact with solutions of known conductivity and obtaining conductivity measurements. The calibration can take into account factors such as the resistivity of the material of the sheath.

Suitable materials for the sheath have been found to have an effective pore size of at least about 0.5 nm, more preferably greater than about 2 nm, for example about 3 nm. Preferably, the effective pore size of the material of the sheath is not more than about 15 nm, more preferably less than about 10 nm, for example about 5 nm. A small pore size can help to provide an effective barrier against contaminants, especially bacteria and viruses.

A preferred method for measurement of pore size involves use of solutions of polyethylene glycol molecules which differ from one another in respect of the molecular weights of the molecules. The solutions are pressurised against the membrane. Variations in the ability of the sheath material to allow the solution to pass through it depend on the molecular weight of the polyethylene glycol. A suitable measurement technique is disclosed in J Envir Engrg, Volume 128 Issue 5, pages 399 to 407 (May 2002).

The material of the sheath at the closed end in the vicinity of the electrodes can be different from the material of the sheath in other parts thereof. At least a portion of the wall of the sheath can be formed from an impermeable material. While it can be preferred for the walls of the sheath to be formed from one material, different materials can be used in different portions of the sheath.

The end of the probe on which the electrodes are provided is located within the sheath cavity prior to the sheath being placed in contact with a tissue sample. Preferably, at least a portion of the sheath is composed of a non-electrically conductive material having a porous structure which when contacted with a tissue sample allows the sheath to be impregnated with an aqueous solution which permits ionic conduction between the electrodes on the probe and the tissue sample. Alternatively, at least a portion of the sheath is composed of an electrically conductive material which has a greater resistivity than the tissue sample and provides a conductive path through the sheath between the electrodes and the tissue sample.

The sheath has the advantage that it can be easily fitted over the probe without requiring the sheath to be aligned with the electrical contacts present on the probe so as to form an electrical connection between the probe and the sheath. Furthermore, the sheath of the present invention has the advantage that the sheath makes electrical contact with a greater area of tissue than the prior art sheaths which have a plurality of electrodes spaced over the surface of the sheath. The electrical impedance of the tissue sample can therefore be measured over the entire area of tissue which is in contact with the sheath. The apparatus of the present invention therefore has improved sensitivity and specificity compared with constructions known previously, for example from WO-98/41151.

The dimensions of the sheath of the present invention depend on the dimensions of the probe which is to be covered. The sheath of the present invention preferably has a diameter of at least about 3 mm, more preferably at least about 5 mm, for example 6 mm. Preferably the diameter of the sheath is less than about 15 mm, more preferably less than about 10 mm, for example 8 mm. Preferably the sheath has a length of at least about 100 mm, more preferably at least about 125 mm, for example 150 mm. The length of the sheath is preferably less than about 250 mm, more preferably less than about 200 mm, for example 175 mm.

The sheath should preferably be a close fit on the probe. It can be preferred for the sheath to be a tight fit on the probe in the vicinity of the electrodes so that the electrodes are wetted by the solution which impregnates the sheath which is composed of a non-electrically conductive porous material so as to provide a conductive path between the electrodes and the tissue sample. Alternatively, it is preferred for the sheath to be a tight fit on the probe in the vicinity of the electrodes so that the electrodes are contacted with the electrically conductive sheath. It can also be preferred for the sheath to be a close fit on the probe at the open end of the sheath, so as to minimise ingress of material (especially contaminants) on to the surface of the probe within the sheath.

The probe can comprise a handle and a shaft. The handle of the probe is attached to the proximal end of the shaft. The shaft will often have a generally constant cross-section. The cross-section of the shaft (which might vary along its length) will generally be less than the cross-section of the handle. The cross-section of the handle might vary along its length, for example to facilitate secure handling by a user. In particular, the handle can be shaped so that it fits comfortably into a user's hand.

The electrodes will generally be arranged at or close to the end of the shaft. They can be provided on an end face of the probe so that they are directed at least partially away from the handle region of the probe. The electrodes can be provided on a side wall of the probe. The location of the electrodes will be selected according to the configuration of the tissue sample which is being examined.

Preferably, the sheath is used to cover at least the end of the probe where the electrodes are located. The sheath should preferably cover all of the surfaces of the probe which will be in contact with a patient's tissue sample during the examination procedure, at least those surfaces of the patient's tissue on which there are body fluids. Accordingly, the sheath preferably covers the probe tip and at least a portion of the probe shaft, especially the probe tip and the entire length of the probe shaft.

The sheath should be secured in place on the probe so that it does not become loose or otherwise dislodged during the examination of the patient's tissue. The material from which the sheath is formed can have elastic properties which can be relied on to help to secure the sheath on to the probe. A band of an elastic material can be applied over the sheath to secure it to the probe. A clip or other mechanical fastener can be used. The probe can be configured to assist in securing the sheath to the probe. For example, a groove can be provided in the probe for the sheath to deform into, either due to the elastic properties of the material of the sheath, or due to an additional fastener.

A sheath which has been used will preferably be disposed of after use, and then replaced with a new sheath. The present invention has the advantage that the same probe can be used repeatedly without the need to sterilise the probe between patients. The sheath of the present invention is therefore more cost effective than known screening probes or probe sheaths which require sterilisation of the probe or probe sheath or the replacement of the probe.

Preferably, the probe is capable of passing a current of at least about 1 µA peak-to-peak, preferably at least about 10 µA peak-to-peak, for example at least about 20 µA peak-to-peak. Preferably, the probes pass a current of less than about 50 µA peak-to-peak, for example 40 µA peak-to-peak.

In a preferred embodiment, the sheath of the present invention is capable of conducting a current of at least about 10 µA peak-to-peak, preferably at least about 20 µA peak-to-peak, for example at least about 30 µA peak-to-peak. Preferably, the sheath passes a current of less than about 50 µA peak-to-peak, for example 40 µA peak-to-peak.

Preferably, the tubular body of the sheath is in direct contact with at least a portion of the electrically conductive probe. Preferably, the sheath is composed of a water permeable, electrically non-conductive material which provides a number of pores or channels through which aqueous ions are able to diffuse. The diffusion of the water and ions into and through the sheath enables the current from the probe to pass to the tissue sample. If the sheath of the present invention is composed of a non-electrically conductive porous material which allows a large proportion of aqueous ions to diffuse through the sheath, the sheath will have a high electrical conductivity.

If the electrical conductivity of the sheath of the present invention when placed in contact with a tissue sample is greater than the electrical conductivity of the tissue sample the current from the probe will pass through the sheath rather than through the tissue sample.

During use, at least a portion of the sheath is placed in contact with the tissue sample. Preferably, the sheath is composed of a water permeable, electrically non-conductive material which allows aqueous ions to diffuse into the tubular body of the sheath providing an electrical contact between the electrical contacts of the probe and the tissue sample. However, the diffusion of the aqueous ions into the sheath which is composed of a water permeable, electrically non-conductive material occurs over a period of time and therefore there is a settling period associated with the readings of the sheath of the present invention. The settling time is the time required for the measurements made by the apparatus of the present invention to settle so as to provide accurate measurements of the tissue sample. If the portion of the sheath which is in contact with the tissue sample is relatively thick then the diffusion of the ions through the water permeable, electrically non-conductive sheath will be relatively slow and therefore the settling period associated with the sheath will be relatively long. Alternatively, if the portion of the water permeable, electrically non-conductive sheath which is in contact with the tissue sample is relatively thin the settling time will be relatively short. If the probe is covered by a sheath which is relatively thin however the risk of the sheath breaking during use is increased.

The current from the probe must be able to penetrate the tissue sample to a sufficient depth so as to be able to accurately measure the electrical impedance of the tissue sample. The squamous epithelium of the cervix has a thickness of approximately 400 µm. It is therefore preferable that the current from the probe penetrates the epithelium to a depth greater than 400 µm.

Factors affecting the choice of the thickness of the material of the sheath include having a sheath which is sufficiently thick so that the sheath has the toughness to withstand the treatment to which it will be subjected when in use without being damaged to the extent that the probe is exposed to the patient's body fluids. However, it can also be preferred to minimise the thickness of the material of the sheath so that the thickness of the conductive path is minimised. This can help to minimise the time taken for measurements to stabilise.

Preferably, the mean maximum thickness of the portion of the sheath which is in contact with the tissue sample is less than about 100 µm, more preferably less than about 75 µm, for example about 50 µm. Preferably, the mean minimum thickness of the portion of the sheath which is in contact with the tissue sample is more than about 10 µm, more preferably more than about 25 µm, for example 40 µm.

The inner surfaces of the walls of the tubular body of the sheath need not be in contact with the probe. For example, the closed end of the sheath is not in direct contact with the tip of the probe. Preferably, a gap is provided between the distal end of the probe and the inner surface of the tubular body of the sheath. Preferably, a wetting agent is present within the gap between the probe and the inner surface of the tubular body of the sheath so as to enable an electrical contact to be made between the sheath and the probe. Suitable wetting agents include aqueous solutions, such as for example salt solutions.

The sheath of the present invention can be composed of any suitable material having the properties discussed above. Preferably, the material of the sheath should be physically stable under the conditions to which it is exposed during use, for example at physiological temperatures. Preferably, the water permeable, electrically non-conductive material which is used at least at the closed end of the sheath includes at least one of cellulose acetate, polyethersulphone, polyamide and cellulose. Preferably, the electrically conductive material which is used at least at the closed end of the sheath includes at least one carbon loaded biocompatible materials. Suitable materials for forming the sheath of the invention include the cellulose based polymer materials sold by Medicell International Limited under the trade mark Visking and sold by Membrana GmbH under the trade mark Cuprophan.

The natural cellulose based polymer material sold under the trade mark Visking has a molecular weight cut-off (MWCO) range from 12000 to 14000. This cellulose based polymer material is stable at a temperature of 60° C. but will distort at approximately 120° C.

The natural cellulose based membrane sold under the trade mark Cuprophan has a molecular weight cut-off of about 10000 Daltons. Cuprophan is known to have good mechanical strength. Furthermore, due to the high suppleness of the material the risk of perforation of Cuprophan is reduced. Cuprophan is an unmodified cellulosic dialysis membrane manufacture by Membrana GmbH covering all basic requirements of standard dialysis treatment.

DETAILED DESCRIPTION OF THE INVENTION

Figure 1:
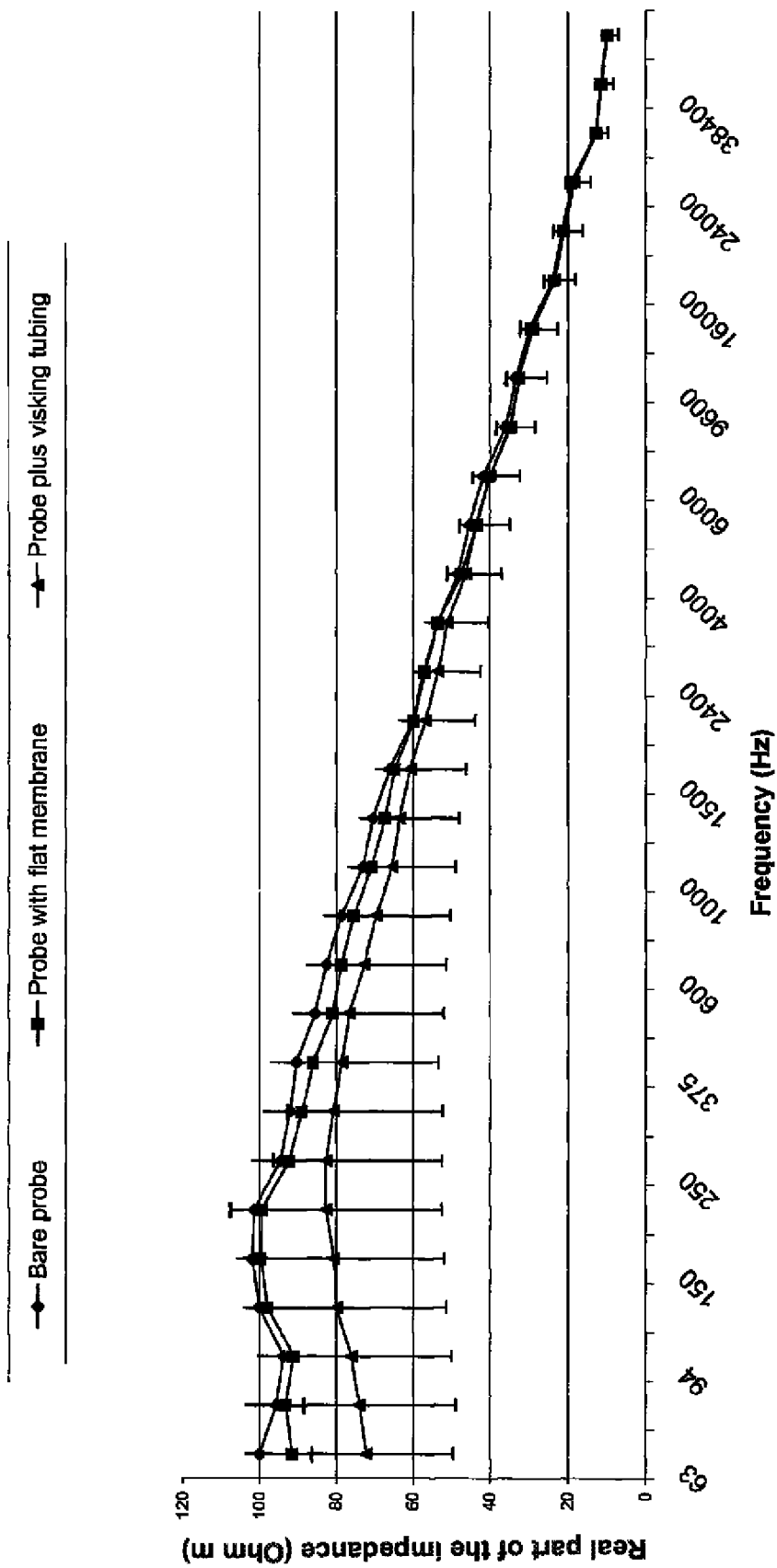
FIG. 1 depicts the results of tests using a probe together with a natural cellulose based membrane to measure the impedance of a cucumber at various frequencies.

The present invention can be used to measure the electrical impedance of a cell sample to detect the presence of abnormal cells. The present invention can also be used to detect other conditions of a patient. For example, the onset of labour is accompanied by changes in tissue impedance which can be identified by such measurements. It has also been found that there is a noticeable difference in the electrical impedance of cervical tissues of pregnant women and women who are not pregnant. The present invention can therefore be used to diagnose obstetrical or non-obstetrical related conditions.

Embodiments of the invention will now be described in the following examples:

EXAMPLE 1

Electrical Conductivity

Preliminary electrical measurements were carried out on a range of membrane materials including cellulose acetate, polyethersulphone (PES), polyamide (nylon) and cellulose. Samples of natural cellulose based membranes sold under the trade marks Visking and Cuprophan were then selected for further electrical measurements. The sample of natural cellulose based membrane sold under the trade mark Visking is in the form of tubing. The properties of the samples of natural cellulose based membranes sold under the trade marks Visking and Cuprophan are illustrated in table 1.

TABLE 1

| Material | Type | Thickness (μm) | Width (mm) | Length (mm) | MWCO (Daltons) | Normal use |
|---|---|---|---|---|---|---|
| Cuprophan ™ | Flat sheet | 11.5 | 250 | 250 | 10,000 | Dialysis |
| Visking ™ | Tubing | 75.8 ± 5.7 | 10 flat | | 600 | 12-14,000 | Dialysis |

The measurement of the thickness of the sample of the natural cellulose based membrane sold under the trade mark Visking is a mean of twelve measurement made using a micrometer. The other data has been supplied by the manufacturer.

The first set of electrical measurements were carried out directly on samples of natural based cellulose materials sold under the trade marks Visking and Cuprophan which were placed between metal clamps. The second set of electrical measurements were made using a tetrapolar probe placed firstly in saline solutions and secondly on cucumber. A sample of the natural cellulose based membrane sold under the trade mark Visking or Cuprophan was then placed between the probe and the saline solutions or cucumber.

Cucumber was used as a test material as cucumber is a convenient test object which has a cellular structure and therefore a characteristic electrical impedance spectrum.

a) Membrane Measurements

Edge-to-edge measurements were obtained from a rectangular piece of each sample which was clamped at opposite ends between an aluminium plate and a PTFE holder. Face-to-face measurements were obtained by sandwiching a rectangular piece of each sample between two brass plates.

The equivalent combination of resistance R and capacitance C presented by each sample were measured using a Wayne Kerr Precision Analyser type 6425 at frequencies between 2 kHz and 20 kHz.

The samples were first measured when dry. The samples were then washed in warm water for 6 minutes and the measurements were taken again. The samples were then submerged in 5% physiological saline for at least 1 minute before a further reading was taken.

The results from two sets of experiments are shown in tables 2 and 3.

TABLE 2

| Material | Geometry | Condition | Width (mm) | Length (mm) | Thick (µm) | C(pF) 2 kHz | C(pF) 20 kHz | R(kΩ) 2 kHz | R(kΩ) 20 kHz |
|---|---|---|---|---|---|---|---|---|---|
| Cuprophan | face-face | Dry | 10.0 | 10.0 | 15.7 | 60 | 57 | ∞ | ∞ |
| Cuprophan | face-face | Washed | 10.0 | 10.0 | 25.3 | 97 | 13 | 0.91 | 0.62 |
| Cuprophan | face-face | Saline | 10.0 | 10.0 | 27.3 | 1397 | 153 | .0.31 | 0.022 |
| Cuprophan | edge-edge | Dry | 30.0 | 30.0 | 15.7 | 1 | 1 | ∞ | ∞ |
| Cuprophan | edge-edge | Washed | 28.0 | 30.0 | 25.3 | 2 | 2 | 540 | 579 |
| Cuprophan | edge-edge | Saline | 28.0 | 30.0 | 33.3 | 6 | 2 | 141 | 159 |
| Visking | face-face | Dry | 8.8 | 10.0 | 77.3 | 31 | 26 | ∞ | ∞ |
| Visking | face-face | Washed | 8.8 | 10.0 | 120 | 50 | 12 | 3.0 | 1.0 |
| Visking | face-face | Saline | 8.8 | 10.0 | 119 | 937 | 88 | 0.031 | 0.023 |
| Visking | edge-edge | Dry | 19.3 | 30.0 | 77.3 | 2 | 6 | ∞ | ∞ |
| Visking | edge-edge | Washed | 19.7 | 30.0 | 120 | 3 | 2 | 438 | 341 |
| Visking | edge-edge | Saline | 19.7 | 30.0 | 119 | 19 | 2 | 29 | 29 |

TABLE 3

| Material | Geometry | Condition | Thickness (µm) | Impedance (Ω) | Impedance phase (deg) | Resistivity (Ωm) | Permittivity |
|---|---|---|---|---|---|---|---|
| Cuprophan | face-face | Dry | 15.7 | ∞ | 89.9 | ∞ | 1.1 |
| Cuprophan | face-face | Washed | 25.3 | 910 | 0.1 | 5796 | 27.7 |
| Cuprophan | face-face | Saline | 27.3 | 31 | 0 | 122 | 43.0 |
| Cuprophan | edge-edge | Dry | 15.7 | ∞ | 85.5 | ∞ | — |
| Cuprophan | edge-edge | Washed | 25.3 | 540k | 0.8 | 12.7 | — |
| Cuprophan | edge-edge | Saline | 33.3 | 141k | 0.6 | 4.4 | — |
| Visking | face-face | Dry | 77.3 | ∞ | 89.9 | ∞ | 3.0 |
| Visking | face-face | Washed | 120 | 3k | 0.1 | 2200 | 7.7 |
| Visking | face-face | Saline | 119 | 31 | 0 | 22.9 | 14.3 |
| Visking | edge-edge | Dry | 77.3 | ∞ | 87.7 | ∞ | — |
| Visking | edge-edge | Washed | 120 | 438k | 0.9 | 34.5 | — |
| Visking | edge-edge | Saline | 119 | 29k | 0.4 | 2.3 | — |

Electrical measurements were made on membrane samples. The results shown in table 3 are the mean of measurements made on three samples. Resistivities greater than 1 MΩm and impedances greater than 1 MΩ are shown as ∞. Impedance measurements were made at a frequency of 2 kHz.

The dry samples are non-conductive. The 'face to face' capacitance of the sample should simply reflect the thickness and permittivity of the samples. The relative permittivity may be calculated from the thickness and area of the sample. The calculated relative permittivity of the sample of natural cellulose based membrane sold under the trade mark Visking is 6 whereas the calculated relative permittivity of the natural cellulose based membrane sold under the trade mark Cuprophan is 1.

The resistivities can be calculated knowing the distance between the electrodes and the cross-sectional area of the membrane. The resistivities of the two samples at 20 kHz following washing with water are 833 Ωm (face-to-face) and 26.9 Ωm (edge-to-edge) for the sample of natural cellulose based membrane sold under the trade mark Visking and 2450 Ωm (face-to-face) and (edge-to-edge) 14.6 Ωm for the sample of natural cellulose based membrane sold under the trade mark Cuprophan.

After immersion in 5% saline solution the resistivities of the two materials are 19.3 Ωm (face-to-face) and 2.27 Ωm (edge-to-edge) for the sample of natural cellulose based membrane sold under the trade mark Visking and 80.6 Ωm (face-to-face) and 4.0 Ωm (edge-to-edge) for the sample of natural cellulose based membrane sold under the trade mark Cuprophan.

b) Measurements Made on Cucumber

A tetrapolar probe having a diameter of 5.5 mm was used. An AC current of 20 µA peak-to-peak was applied between a pair of electrodes and the resulting potential measured between the remaining two electrodes. Measurements were made over the frequency range of from 63 Hz to 64.5 kHz.

The cucumber was freshly sliced with a thickness of 10 mm. The spectral measurements were made by placing the face of the probe approximately half way between the centre and the edge of the cucumber. The samples were then each placed between the probe and the cucumber. Twelve measurements were made on the cucumber using 10×10 mm samples of the natural cellulose based membrane sold under the trade marks Visking or Cuprophan. The measurements were taken after the measurements had settled. The results are shown in FIG. 1.

The results using the sample of the natural cellulose based membrane sold under the trade mark Cuprophan are almost indistinguishable from the measurements of the electrical impedance made by the probe without any membrane present. The measurements of the electrical impedance made using the sample of the natural cellulose based membrane sold under the trade mark Visking are lower than the measurements made by the probe without a sheath at low frequencies. This difference may be because the sample of the natural cellulose based membrane sold under the trade mark Visking is relatively thick and therefore there will be a shunt current. The sensitivity of the sheathed probe to the cucumber tissue will therefore be reduced when compared to the measurements of the unsheathed probe as the probe is further from the cucumber.

c) Settling Times

Twelve measurements were made at different points on the cucumber using samples of natural cellulose based membranes sold under the trade mark Visking and Cuprophan. The time for the measurements of the electrical impedance to settle was observed. The means and standard deviations for these settling times are shown in table 4.

TABLE 4

| Condition | Thickness (μm) | Settling time (s) |
| --- | --- | --- |
| Unsheathed probe | 0 | 8.0 ± 5.2 |
| Cuprophan ™ sheath | 18.3 ± 6.1 | 6.6 ± 2.4 |
| Visking ™ sheath | 75.8 ± 5.7 | 46.9 ± 5.2 |

It can be seen that the settling time was not increased by the presence of the sample of the natural cellulose based membrane sold under the trade mark Cuprophan. However, the settling time is about 8 seconds even when using an unsheathed probe. A much longer settling time (46.9 seconds) is observed for the probe having a sheath composed of a natural cellulose based membrane sold under the trade mark Visking. It was also noted that the settling times increased at lower frequencies.

After these tests had been performed, the probe having a sheath composed of a natural cellulose based membrane sold under the trade mark Visking was used to measure a further 12 points on the cucumber. The mean settling time for this set of measurements was observed to be 16.1±7.9 seconds. This is considerably less than the mean settling time for the first set of measurements.

d) Measurements on Saline Solutions

Measurements on saline solutions were made by clamping the probe above the solution and then lowering it until it just made contact with a saline solution. The samples of the natural cellulose based membranes sold under the trade marks Cuprophan and Visking were then each placed over the end of the probe before the probe contacts the fluid. The samples were held in place against the probe with a rubber O-ring. The measurements were performed at a frequency of 9.6 kHz.

The saline solutions had varying conductivities within the range which would be expected on cervical tissue. The results are illustrated in Tables 5 and 6.

TABLE 5

| Expected resistivity (Ωm) | Measured resistivity (Ωm)- unsheathed probe | Measured resistivity (Ωm)- Cuprophan ™ | Measured resistivity (Ωm)- Visking ™ |
| --- | --- | --- | --- |
| 80.6 | 64.1 | 53.5 | 23.1 |
| 41.8 | 39.3 | 22.2 | 22.1 |
| 20.8 | 23.3 | 17.8 | 13.4 |
| 10.0 | 9.7 | 11.0 | 8.1 |
| 5.2 | 4.9 | 5.2 | 8.0 |
| 2.6 | 2.6 | 2.7 | 4.6 |

TABLE 6

| Expected resistivity (Ωm) | Measured resistivity (Ωm)- unsheathed probe | Measured resistivity (Ωm)- Cuprophan ™ | Measured resistivity (Ωm)- Visking ™ |
| --- | --- | --- | --- |
| 80.6 | 64.0 | 51.6 | 21.9 |
| 41.8 | 38.8 | 26.5 | 22.5 |
| 20.8 | 23.5 | 17.2 | 13.3 |
| 10.0 | 9.8 | 10.3 | 8.2 |
| 5.2 | 5.0 | 5.2 | 8.0 |
| 2.6 | 2.6 | 2.7 | 4.4 |

Measurements were made using a probe placed in contact with a saline solution. The measured resistivities are presented as the mean across the 30 frequencies between 63 Hz and 48 Hz. All measurements made using a membrane are significantly different (p<0.05) from those made using the bare probe.

When the probe is sheathed in a sample of a natural cellulose based membrane sold under the trade mark Visking™ appears to produce measurements which are underestimates of the true resistivity of the saline solution at high resistivities (>10 Ωm). The underestimates may be caused by a shunting of current in the sample of the natural cellulose based membrane sold under the trade mark Visking. The sample of the natural cellulose based membrane sold under the trade mark Visking also produces overestimates of the true resistivity of the solution at low resistivities (<10 Ωm) which could be due to the thickness of the tubing.

The sample of natural cellulose based membrane sold under the trade mark Cuprophan also produces some underestimation of the true resistivity of the solution at high resistivities (greater than 20.8 Ωm).

EXAMPLE 2

Infection Control Measurements

The ability of the samples of natural cellulose based membranes sold under the trade marks Visking and Cuprophan to block the passage of polio vaccine was tested. The sample of natural cellulose based membrane sold under the trade mark Visking is sold in the form of tubing.

A portion of the sample of the natural cellulose based membrane sold under the trade mark Visking was placed within a chamber containing 10 ml of PBS (phosphate buffer solution). 2 ml of PBS were placed within the inner region of the sample of the natural cellulose based membrane sold under the trade mark Visking. 3 drops of a polio vaccine were added to the inner region of the sample of natural cellulose based membrane sold under the trade mark Visking and gently mixed with the PBS. The test sample was left overnight. Two aliquots of dialsyate were taken from the outer chamber and one aliquot was taken from the inner chamber for qualitative enterovirus PCR (polymerase chain reaction) testing.

The sample of natural cellulose based membrane sold under the trade mark Cuprophan was tested by mounting the sample between two chambers of a perspex unit. 50 ml sterile PBS was placed on either side of the sample. One dose of a polio vaccine was added to the right hand side chamber of the unit. The test sample was left overnight. Three aliquots of dialysate were taken from the left hand side unit and one aliquot was taken from the right hand side unit for quantitative enterovirus PCR testing.

The aliquots were sent to a reference laboratory for PCR testing. No enterovirus RNA was detected as having passed through either of the samples of the natural cellulose based membrane sold under the trade marks Visking tubing or the Cuprophan membrane. The concentration of enterovirus RNA detected on the infection side of the sample of the natural cellulose based membrane sold under the trade mark Visking was 900000 TCID 50 per ml. The concentration of enterovirus RNA detected on the infection side of the Cuprophan membrane was 100000 TCID 50 per ml.

The invention claimed is:

1. An apparatus configured to measure the electrical impedance of a tissue sample, wherein the apparatus comprises:
    (a) an elongate probe having electrodes at one end, wherein the electrodes are configured to transmit an electrical signal between the apparatus and the tissue in contact with the apparatus; and
    (b) a sheath removably disposed on the elongate probe, the sheath comprising an elongate tubular body having a closed end and an open end and defining an internal cavity, in which the end of the probe on which the electrodes are provided is received within the cavity, and in which at least a portion of the sheath is formed from a material which is capable of providing a conductive path through the sheath between the electrodes and the tissue sample when the sheath is contacted with the tissue sample, and in which the resistivity of the material when the material is contacted with the tissue sample is greater than the resistivity of the tissue sample, and in which the material of the sheath is formed from a polymeric material which has a porous structure such that in use the polymeric material can be impregnated with body fluid to provide an ionically conductive path through the sheath between the electrodes and the tissue sample, and in which the porous material has a pore size effective to block the passage of the polio virus through the porous material, wherein the sheath is removable from the probe after use, such that the probe is configured to be covered with another sheath and used on another patient without requiring sterilization of the probe.

2. The apparatus as claimed in claim 1, in which the sheath is composed of one or more materials selected from cellulose acetate, polyethersulphone, polyamide, and cellulose.

3. The apparatus as claims in claim 1, which includes a quantity of an aqueous solution of a salt between the electrodes and the sheath.

4. The apparatus as claimed in claim 1, in which the material of the sheath at the closed end in the vicinity of the electrodes is different from the material in other parts of the sheath.

5. The apparatus as claimed in claim 1, wherein the ratio of the resistivity of the material of the sheath, when impregnated with body fluid, to the resistivity of the tissue sample is at least about 10.

6. An apparatus configured to measure the electrical impedance of a tissue sample, wherein the apparatus comprises:

(a) an elongate probe having electrodes at one end, wherein the electrodes are configured to transmit an electrical signal between the apparatus and the tissue in contact with the apparatus; and (b) a sheath removably disposed on the elongate probe, the sheath comprising an elongate tubular body having a closed end and an open end and defining an internal cavity, in which the end of the probe on which the electrodes are provided is received within the cavity, and in which at least a portion of the sheath is formed from a material which is capable of providing a conductive path through the sheath between the electrodes and the tissue sample when the sheath is contacted with the tissue sample, and in which the resistivity of the material when the material is contacted with the tissue sample is greater than the resistivity of the tissue sample, in which the material of the sheath is inherently electronically conductive, wherein the sheath is removable from the probe after use, such that the probe is configured to be covered with another sheath and used on another patient without requiring sterilization of the probe.

7. The apparatus as claimed in claim 6, in which the material of the sheath at the closed end in the vicinity of the electrodes is different from the material in other parts of the sheath.

8. The apparatus as claimed in claim 6, wherein the ratio of the resistivity of the material of the sheath to the resistivity of the tissue sample is at least about 10.

9. The apparatus as claimed in claim 6, in which the sheath is composed of carbon loaded biocompatible material.

* * * * *